(12) United States Patent
Ghelmansarai et al.

(10) Patent No.: US 7,263,164 B2
(45) Date of Patent: Aug. 28, 2007

(54) IMAGING SYSTEM TO COMPENSATE FOR X-RAY SCATTER

(75) Inventors: Farhad A. Ghelmansarai, Danville, CA (US); Johannes Stahl, Walnut Creek, CA (US); Dieter Manthey, Clayton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 145 days.

(21) Appl. No.: 10/837,405

(22) Filed: Apr. 30, 2004

(65) Prior Publication Data

US 2005/0243963 A1 Nov. 3, 2005

(51) Int. Cl.
*G01N 23/201* (2006.01)
(52) U.S. Cl. .............................. 378/87; 378/7; 378/98.4
(58) Field of Classification Search ................. 378/6, 378/7, 18, 98.12, 207, 70, 86, 87, 98.4, 901, 378/12
See application file for complete search history.

(56) References Cited

U.S. PATENT DOCUMENTS 4,727,562 A * 2/1988 Belanger ................... 378/98.4
5,635,709 A * 6/1997 Sliski et al. ................ 250/252.1
6,369,389 B1 * 4/2002 Berlad et al. .............. 250/363.07
6,636,622 B2 * 10/2003 Mackie et al. ............... 382/132
2004/0101108 A1 * 5/2004 Charleton ..................... 378/198
2004/0228435 A1 * 11/2004 Russell ......................... 378/18
2004/0252810 A1 * 12/2004 Tsujii .......................... 378/207

FOREIGN PATENT DOCUMENTS

EP 105618 A2 * 4/1984
EP 660599 A1 * 6/1995
EP 689047 A1 * 12/1995

* cited by examiner

Primary Examiner—Edward J. Glick
Assistant Examiner—Anastasia S. Midkiff (57) ABSTRACT

A system includes acquisition of a first image of a first radiation field, at least a portion of the first radiation field comprising radiation attenuated by a device, and the first image including a representation of first scatter radiation generated during acquisition of the first image, acquisition of a second image of a second radiation field, at least a portion of the second radiation field comprising radiation attenuated by a volume corresponding to the device, and the second image including a representation of second scatter radiation generated during acquisition of the second image, and modification of the second image based on the first image to compensate for the second scatter radiation.

29 Claims, 10 Drawing Sheets

IMAGING SYSTEM TO COMPENSATE FOR X-RAY SCATTER

BACKGROUND

1. Field

The present invention relates generally to the effects of scatter radiation on radiation imaging devices, and may be applied, for example, to portal imaging in conjunction with radiation therapy.

2. Description

Some conventional imaging devices can acquire images that represent incident X-ray radiation. For example, amorphous selenium-based imaging devices convert received X-ray radiation to stored electrical charge that represents an intensity distribution of the X-ray radiation. Other imaging devices may include a scintillator layer that receives X-ray radiation and emits light in proportion to the intensity of the received radiation. An array of charge-coupled devices or photodiodes receives the light emitted by the scintillator layer and stores electrical charge in proportion to the intensity of the received light. In either case, the stored electrical charge may be used to generate an image that represents the received X-ray radiation.

Portions of the received radiation may be attenuated by objects disposed between the imaging device and a source of the radiation. Consequently, the received radiation and the acquired image will include areas of different intensities that reflect different compositions of the objects. For example, areas of low radiation intensity may represent bone and areas of high radiation intensity may represent tissue. Images acquired using X-ray radiation may be used to diagnose illness, to plan radiation therapy, to confirm patient positioning prior to therapy, and/or to confirm a shape and intensity distribution of a radiation field prior to therapy.

The foregoing imaging techniques may generate scatter radiation. Some of this scatter radiation may be represented in the images acquired thereby. The scatter radiation may reduce the intensity gradients (i.e. contrast) between image areas that represent different objects, and/or reduce the signal-to-noise ratio of the acquired images. Accordingly, it would be beneficial to provide improved image quality by addressing the issue of scatter radiation.

SUMMARY

To address at least the above problems, some embodiments provide a system, method, medium, apparatus, and means to acquire a first image of a first radiation field, at least a portion of the first radiation field comprising radiation attenuated by a device, and the first image including a representation of first scatter radiation generated during acquisition of the first image, to acquire a second image of a second radiation field, at least a portion of the second radiation field comprising radiation attenuated by a volume corresponding to the device, and the second image including a representation of second scatter radiation generated during acquisition of the second image, and to modify the second image based on the first image to compensate for the second scatter radiation.

According to further aspects, a third image of a third radiation field is acquired, at least a portion of the third radiation field comprising radiation attenuated by a second device, and the third image including a representation of third scatter radiation generated during acquisition of the third image, wherein modification of the second image includes modification of the second image based on the first image and the third image to compensate for the second scatter radiation, and wherein a representation of the third scatter radiation differs from a representation of the first scatter radiation. Modification of the second image may include interpolation of the representation of the third scatter radiation and the representation of the first scatter radiation based on radiation attenuation properties of the first device, radiation attenuation properties of the third device, and radiation attenuation properties of the volume to determine a reference scatter image, and modification of the second image based on the reference scatter image.

In some embodiments, modification of the second image includes determination of a conversion to substantially remove the representation of the first scatter radiation from the first image, and application of the conversion to the second image.

The claimed invention is not limited to the disclosed embodiments, however, as those skilled in the art can readily adapt the teachings herein to create other embodiments and applications.

BRIEF DESCRIPTION OF THE DRAWINGS

The exact nature of the claimed invention, as well as its objects and advantages, will become readily apparent from consideration of the following specification as illustrated in the accompanying drawings, in which like reference numerals designate like parts, and wherein:

DETAILED DESCRIPTION

The following description is provided to enable any person skilled in the art to make and use the claimed invention and sets forth the best mode contemplated by the inventors for carrying out the claimed invention. Various modifications, however, will remain readily apparent to those in the art.

Figure 1:
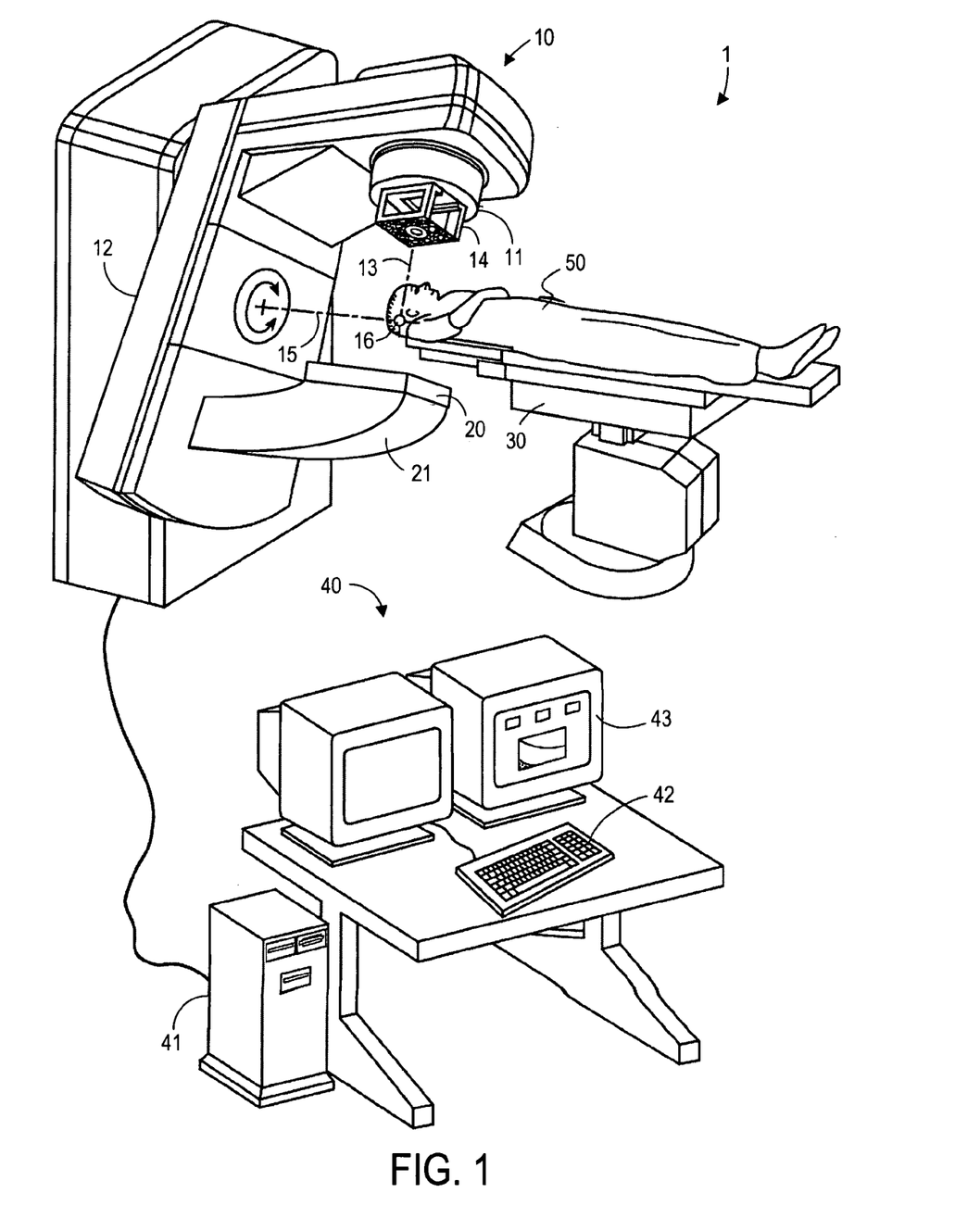
FIG. 1 is a view of a radiation therapy room.

FIG. 1 illustrates radiation therapy room 1 pursuant to some embodiments. Radiation therapy room 1 includes linear accelerator (linac) 10, imaging device 20, table 30 and operator station 40. The elements of radiation therapy room 1 may be used to deliver radiation to patient 50 according to a radiation therapy plan.

Linac 10 generates and emits a radiation beam, and is primarily composed of treatment head 11 and gantry 12.

Treatment head 11 includes a beam-emitting device (not shown) for emitting radiation beam 13 used during calibration, verification, and/or treatment. Radiation beam 13 may comprise electron, photon or any other type of radiation. Radiation beam 13 may comprise megavoltage radiation. In some embodiments, radiation beam 13 comprises kilovoltage radiation having energies ranging from 50 to 150 keV, and an X-ray tube may be substituted for linac 10.

Treatment head 11 also includes is a beam-shielding device, or collimator (not shown) for shaping beam 13 and for shielding sensitive surfaces from the beam. Accessory tray 14 is mounted on treatment head 11 and may be configured to receive and securely hold attachments used during the course of treatment planning and treatment. These attachments may include reticles, wedges, or the like for further defining field sizes and intensities.

Treatment head 11 is fastened to a projection of gantry 12. Gantry 12 is rotatable around gantry axis 15 before, during and after emission of beam 13. Beam 13 is emitted towards isocenter 16, which is a point located at the intersection of gantry axis 15 and a beam axis of beam 13. Due to divergence of radiation beam 13 and the shaping of beam 13 by the aforementioned beam-shaping devices, beam 13 may produce a two-dimensional radiation field on a plane perpendicular to the beam axis and including isocenter 16.

Imaging device 20 acquires images that are used before, during and after radiation therapy. For example, imaging device 20 may be used to acquire images for diagnosis, verification and recordation of a patient position, and verification and recordation of an internal patient portal to which radiation is delivered. As described above, the effectiveness of radiation therapy often depends on the quality of the acquired images.

In some embodiments, imaging device 20 is a flat-panel imaging device using a scintillator layer and solid-state amorphous silicon photodiodes deployed in a two-dimensional array. The RID1640, offered by Perkin-Elmer®, Inc. of Fremont, Calif., is one suitable imaging device. Imaging device 20 may be attached to gantry 12 in any manner, including via extendible and retractable housing 21.

In operation, the scintillator layer receives X-rays and generates light in proportion to the intensity of the received X-rays. The array of photodiodes receives the light and records the intensity of received light as stored electrical charge. The stored charge therefore comprises an acquired image that represents intensities at each location of a radiation field produced by radiation beam 13. The bounds of the radiation field are determined by the physical intersection of the radiation beam with the surface of the scintillator layer.

Imaging device 20 may comprise other types of imaging devices. For example, X-ray radiation may also be converted to and stored as electrical charge without use of a scintillator layer. In such imaging devices, x-rays are absorbed directly by an array of amorphous selenium photoconductors. The photoconductors convert the x-rays directly to stored electrical charge that comprises an acquired image of a radiation field. Imaging device 20 may also comprise a CCD or tube-based camera. Such an imaging device may include a light-proof housing within which are disposed a scintillator, a mirror, and a camera.

Table 30 supports patient 50 during radiation therapy. Table 30 is adjustable to ensure, along with rotation of gantry 12, that a volume of interest is positioned between treatment head 11 an imaging device 20. Table 30 may also be used to support radiation attenuation devices used for acquisition of correction images, other calibration tasks and/or beam verification.

Operator station 40 includes processor 41 in communication with an input device such as keyboard 42 and an operator console 43 (including one or more visual display units or monitors). Operator station 40 is typically operated by an operator who administers actual delivery of radiation therapy as prescribed by an oncologist. Operator station 40 may be located apart from linac 10, such as in a different room, in order to protect the operator from radiation. For example, linac 10 may be located in a heavily shielded room, such as a concrete vault, which shields the operator from radiation generated by linac 10.

The operator may use keyboard 42 to control linac 10 and imaging device 20 so as to acquire desired images. The acquired images may be stored in a data storage device of processor 41. Operator console 43 may display acquired image data to the operator before, during and after therapy.

Processor 41 may modify, convert and/or perform transformations on the acquired images according to executable process steps stored in processor 41. In some aspects, the process steps are executed by processor 41, linac 10, imaging device 20, and/or another element to acquire a first image of a first radiation field, at least a portion of the first radiation field comprising radiation attenuated by a radiation attenuation device, and the first image including a representation of first scatter radiation generated during acquisition of the first image, to acquire a second image of a second radiation field, at least a portion of the second radiation field comprising radiation attenuated by a volume corresponding to the radiation attenuation device, and the second image including a representation of second scatter radiation generated during acquisition of the second image, and to modify the second image based on the first image to compensate for the second scatter radiation. In some embodiments, modification of the second image includes determination of a conversion to substantially remove including the representation of the first scatter radiation from the first image, and application of the conversion to the second image.

The process steps may be stored on any medium, including a fixed disk, a floppy disk, a CD-ROM, a DVD-ROM, a Zip™ disk, a magnetic tape, or a signal. Some or all of the process steps may also be stored in one or more devices. Moreover, some or all of the foregoing process steps may be implemented in hardware, such as a hardware card installed in processor 41 and discrete circuitry of imaging device 20.

Each of the devices shown in FIG. 1 may include less or more elements than those shown. In addition, embodiments are not limited to the devices shown in FIG. 1.

Figure 2:
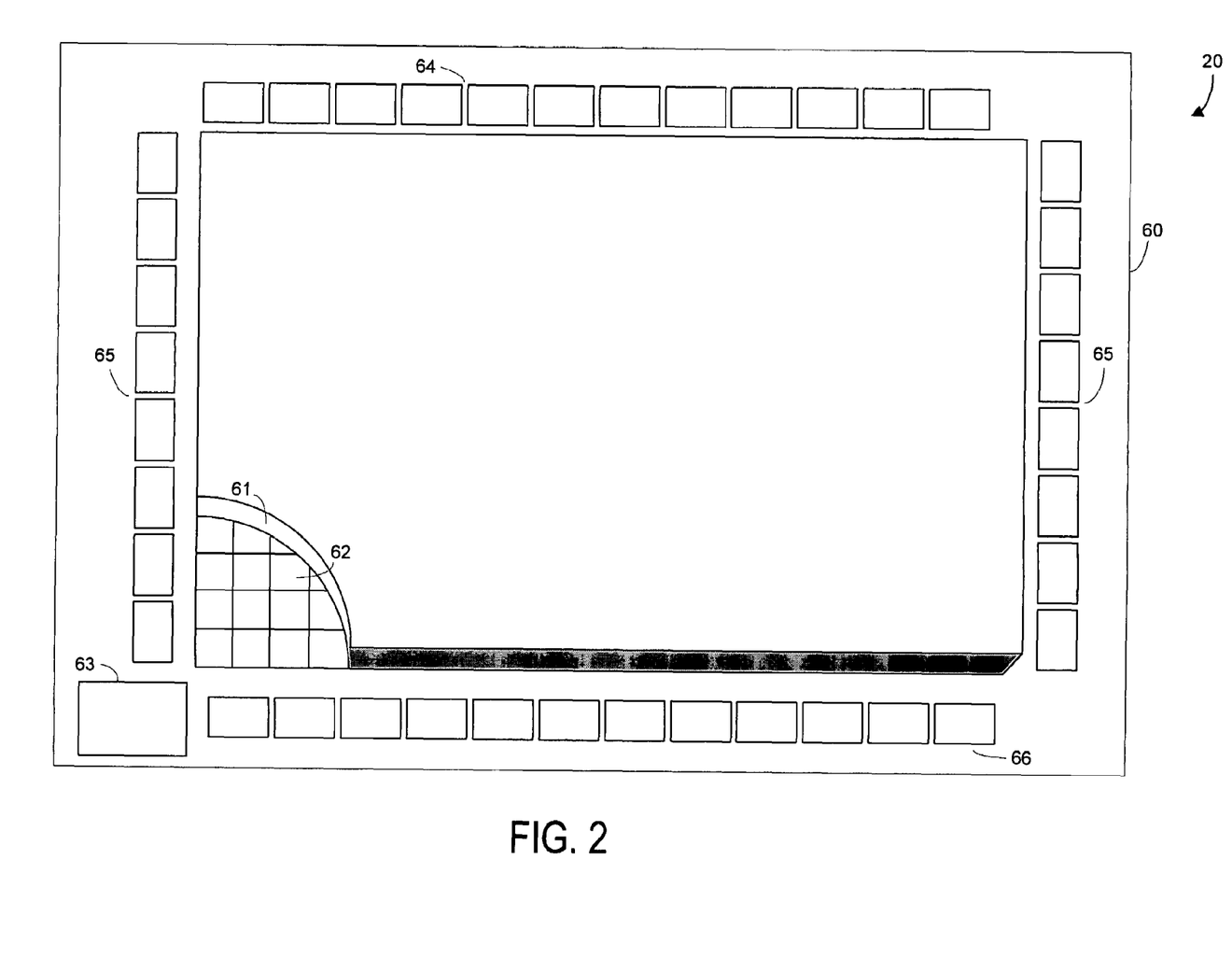
FIG. 2 is a cutaway top view of an imaging device according to some embodiments.

FIG. 2 is a cutaway top view of imaging device 20 according to some embodiments. Imaging device 20 of FIG. 2 is a flat-panel imaging device using solid-state amorphous silicon sensors deployed in a two-dimensional array. As shown, imaging device 20 consists of circuit board 60 on which various elements are mounted. One such element is scintillator 61, a gadolinium-sulfide layer that absorbs X-ray radiation and emits visible photons having an intensity proportional to that of the absorbed X-ray radiation.

The cutaway portion of scintillator 61 shows imaging elements 62. Imaging elements 62 comprise a matrix of amorphous silicon photodiodes and associated thin-film transistors. The matrix extends below the area of scintillator 61 shown in FIG. 2. In some embodiments, the matrix includes 1,048,576 photodiodes arranged in a 1024×1024 pixels array on 400 μm centers. The resulting photoactive region is approximately 41×41 cm$^2$.

Briefly, the photodiodes of imaging elements 62 absorb visible photons generated by scintillator 61. The absorbed photons generate a current that is integrated into the photodiodes' self-capacitance as an electrical charge. The charge is read from the photodiode by applying a signal to a transistor associated with the photodiode. The read charge may be considered image information and used to construct an image.

Timing and control device 63 controls operation of imaging device 20 in accordance with process steps stored therein and commands received from remotely-connected elements. According to some embodiments, timing and control device 63 may control bias devices 64 to apply required bias voltages to the photodiodes of imaging elements 62. Timing and control device 63 may also control the application of signals to appropriate ones of line driver devices 65 to initiate reading the amount of charge, or image information, captured in one or more photodiodes of imaging elements 62. Data and signal amplification devices 66 are then controlled to receive and amplify the image information, which is thereafter multiplexed and converted to digital by timing and control device 63.

Commands and data can be transmitted to and from imaging device 20 via I/O lines (not shown). Moreover, the elements of imaging device 20 shown in FIG. 2 may be encased in a suitable protective housing.

Figure 3:
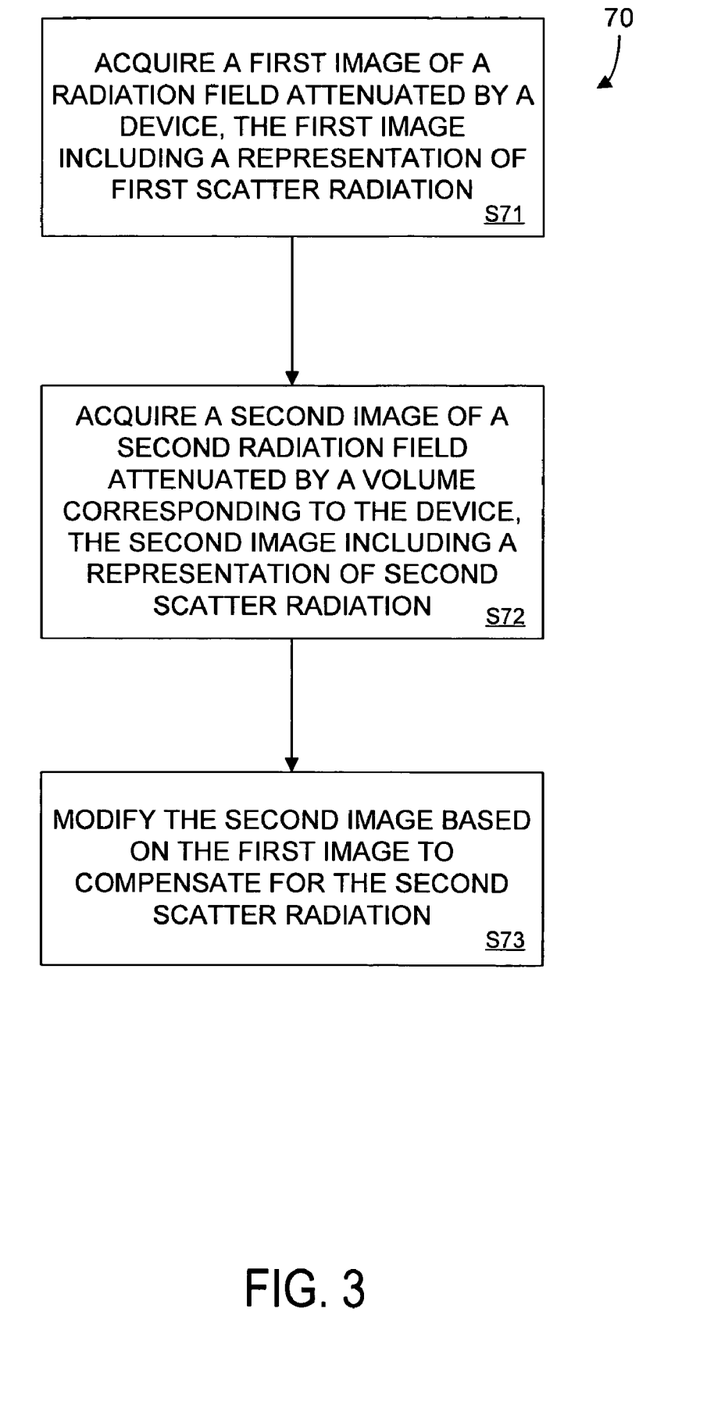
FIG. 3 is a flow diagram of process steps according to some embodiments.

FIG. 3 is a flow diagram of process steps 70 according to some embodiments. Process steps 70 may be embodied, in whole or in part, by hardware of and/or software executed by elements including but not limited to processor 41, linac 10, and imaging device 20.

A first image of a radiation field is initially acquired in step S71. At least a portion of the radiation field is attenuated by a radiation attenuation device. Also, the first image includes a representation of first scatter radiation.

Figure 4:
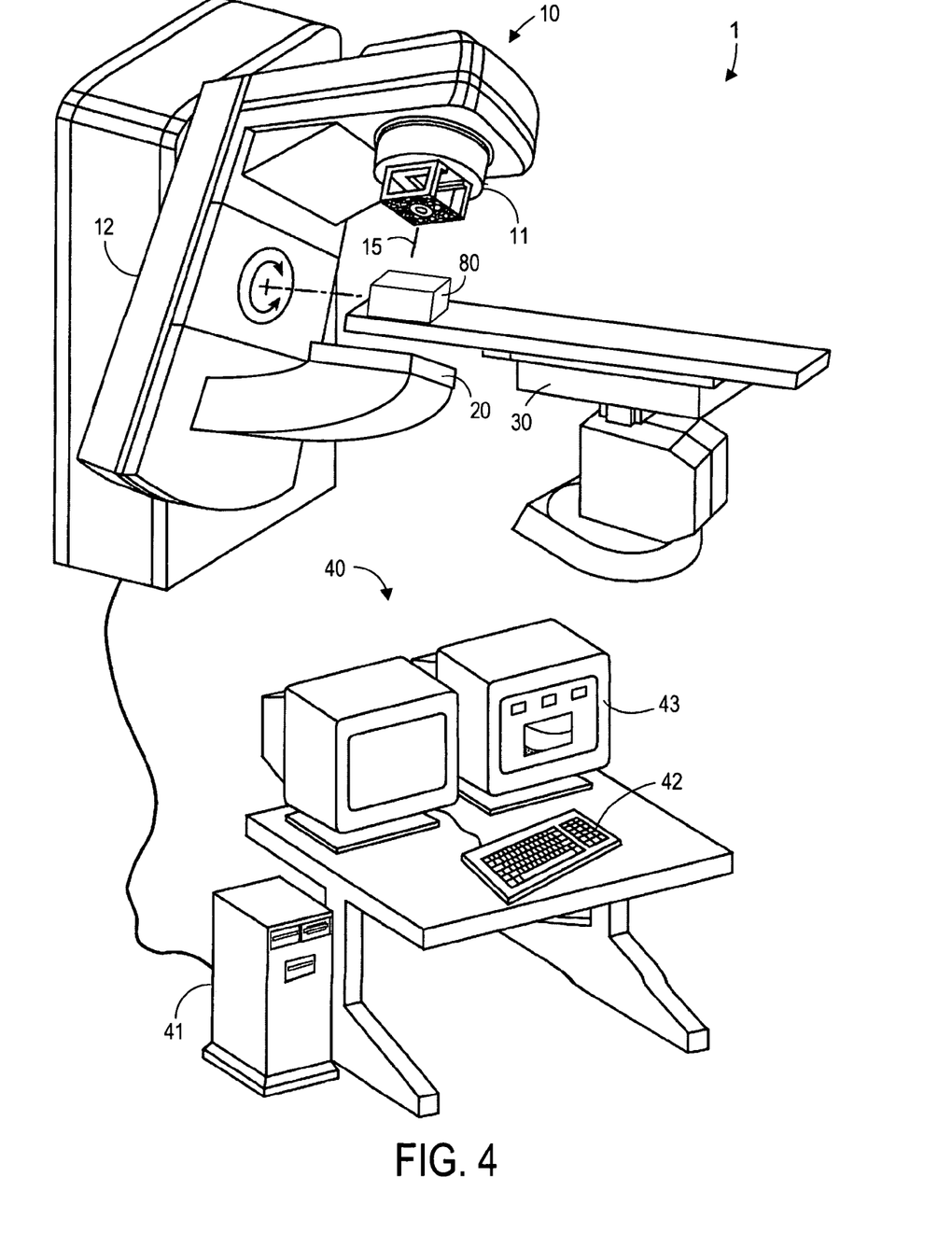
FIG. 4 illustrates acquisition of a first image including a representation of first scatter radiation according to some embodiments.

FIG. 4 illustrates step S71 according to some embodiments. As shown, linac 10 emits radiation beam 15 toward radiation attenuation device 80. Gantry 12 may be positioned in some embodiments such that a beam axis of beam 15 is normal to an upper surface of radiation attenuation device 80. Radiation attenuation device 80 is positioned on table 30 between treatment head 11 and imaging device 20. Due to the divergent nature of beam 15, beam 15 produces the first radiation field on a surface of imaging device 20. Moreover, due to the position of radiation attenuation device 80, a portion of the first radiation field is attenuated by radiation attenuation device 80. In some embodiments, the portion is the entire first radiation field.

Radiation attenuation device 80 comprises a tissue-equivalent phantom such as a water phantom according to some embodiments. In particular, radiation attenuation device 80 may be composed of material having radiation-attentive properties similar to radiation properties of a given volume of tissue. Radiation attenuation device 80 may be composed of material having radiation-attentive properties similar to those of any other volume of interest.

Compton scattering may result from the passing of radiation through radiation attenuation device 80 and other elements of room 1 during step S71. The Compton scattering may produce scatter X-ray radiation. This scatter radiation may be detected by imaging device 20 during step S71 and may therefore be represented in the acquired image.

Figure 5:
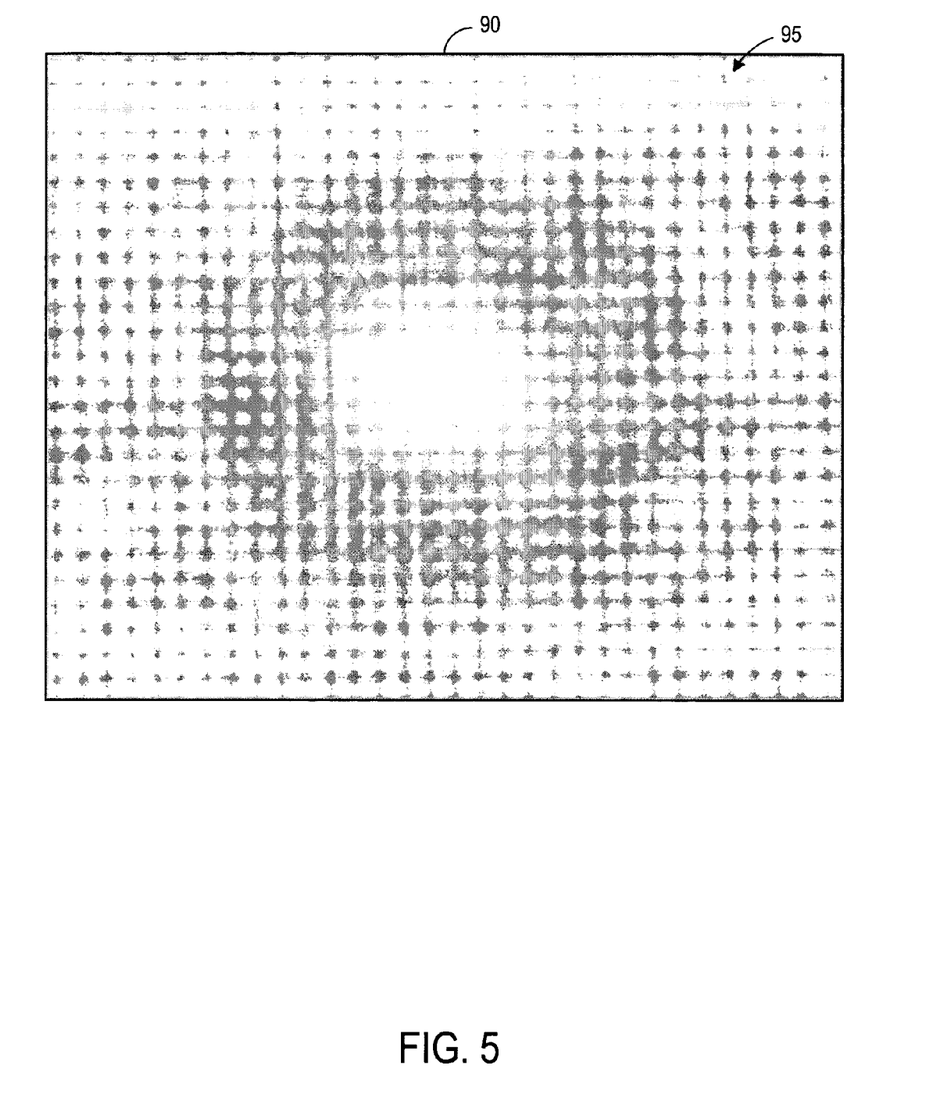
FIG. 5 illustrates a first image of a first radiation field according to some embodiments.

FIG. 5 is a representation of the first image including a representation of first scatter radiation according to some embodiments. Light-colored areas of first image 90 represent greater radiation intensity than dark-colored areas. For simplicity, it will be assumed that the dark and light-colored areas of image 90 comprise representation 95 of first scatter radiation generated during step S71. In this regard, it will be assumed that an intensity of the radiation field produced by beam 15 was uniform, and that all of the radiation of the imaged first radiation field was uniformly attenuated by radiation attenuation device 80. Moreover, image 90 assumes homogeneous gain and dark current effects among the pixels of imaging device 20. Currently- or hereafter-known methods may be used to compensate for beam non-uniformity, non-homogeneous pixel gain and/or non-homogeneous dark current effects according to some embodiments. Some of these embodiments will be described below.

A second image of a second radiation field is acquired in step S72. The second radiation field is attenuated by a volume corresponding to the radiation attenuation device, and includes a representation of second scatter radiation. A correspondence between the radiation attenuation device and the volume may result in a substantial similarity between the second scatter radiation generated by the passing of radiation through the volume and the first scatter radiation of step S71.

FIG. 1 illustrates acquisition of the second image according to some embodiments of step S72. Again, gantry 12 may be positioned in some embodiments of step S72 such that a beam axis of beam 15 is normal to an upper surface of patient 50. The volume of patient 50 disposed between treatment head 11 and imaging device 20 corresponds to radiation attenuation device 80 of FIG. 4. According to some embodiments, the radiation attenuation properties of the volume are substantially similar to the radiation attenuation properties of radiation attenuation device 80.

Figure 6:
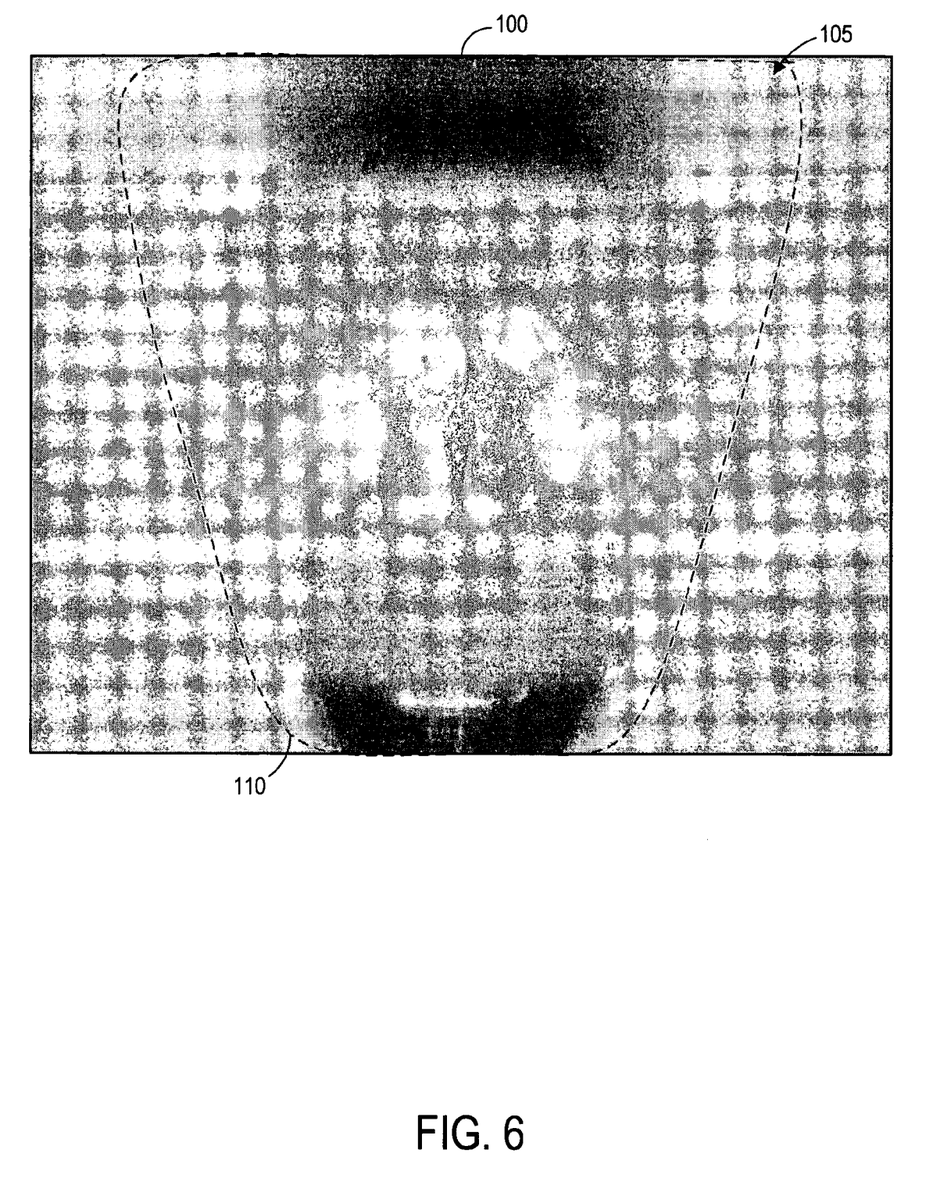
FIG. 6 illustrates a second image of a second radiation field according to some embodiments.

FIG. 6 shows a second image according to some embodiments of step S72. Light-colored areas of second image 100 represent greater radiation intensity than dark-colored areas. An entire portion of second image 100 includes representation 105 of second scatter radiation generated during step S72. Image 100 also includes representation 110 (roughly denoted by the dotted line) of anatomical features of the subject volume of patient 50. For example, light areas of representation 110 may represent structures providing low radiation attenuation intensity and dark areas of representation 110 may represent structures providing higher radiation attenuation.

Returning to process 70, the second image is modified based on the first image in step S73 to compensate for the second scatter radiation. Step S73 may comprise determining a conversion to substantially remove the representation of the first scatter radiation from the first image, and applying the conversion to the second image. According to some embodiments of step S73, an average value of each of a plurality of pixels of the first image is determined, and a gain is determined for each of the plurality of pixels. If applied to the plurality of pixels, the gain would cause each of the plurality of pixels to have a single value. The gain is then applied to each of a corresponding plurality of pixels of the second image.

In some embodiments of step S73, a scatter correction value is determined for each of a plurality of pixels of the first image. If subtracted from (or added to, depending on the convention employed) the plurality of pixels, the scatter correction value would substantially remove the representation of the first scatter radiation from the first image. The scatter correction value is then subtracted from (or added to) each of a corresponding plurality of pixels of the second image.

Figure 7:
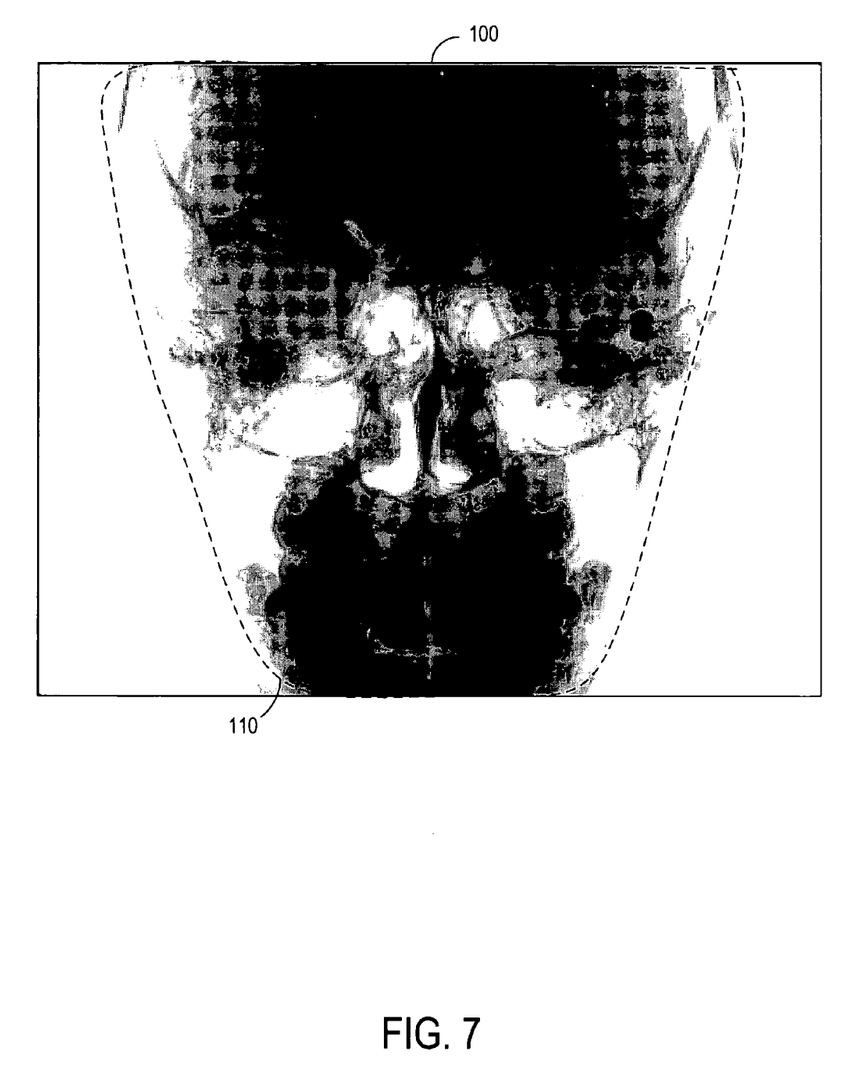
FIG. 7 illustrates a second image after modification according to some embodiments.

The foregoing embodiments of step S73 may remove the representation of the second scatter radiation from the second image in a case that the representation of the first scatter radiation is substantially similar to the representation of the second scatter radiation. FIG. 7 illustrate second image 100 after step S73 according to some embodiments. Compensation for the second scatter radiation has increased the contrast between structures of the representation 110.

Figure 8:
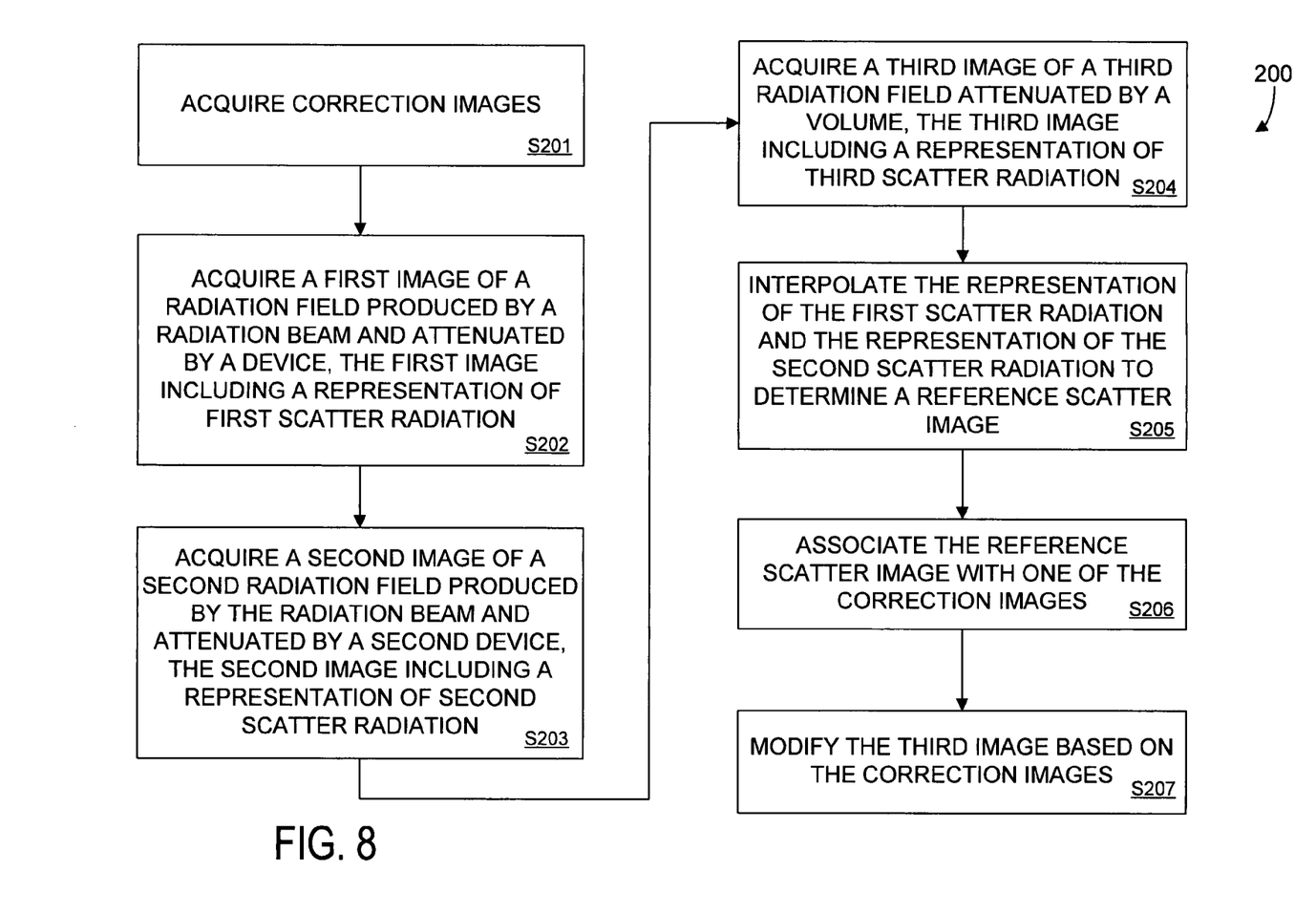
FIG. 8 is a flow diagram of process steps according to some embodiments.

FIG. 8 is a flow diagram of process steps 200 according to some embodiments. Process steps 200 may be used to compensate for X-ray scatter radiation represented in acquired images. Process steps 200 may be embodied, in whole or in part, by hardware of and/or software executed by devices including but not limited to processor 41, linac 10, and imaging device 20.

Initially, correction images are acquired in step S201. The correction images may be acquired anytime before radiation therapy, but are commonly acquired in the early morning prior to the administration of radiation therapy throughout the day. In some embodiments, the acquired correction images include images used for offset correction, gain correction, and dead pixel correction.

Many imaging devices that convert radiation to electrical charge require biasing of their imaging elements. This biasing generates a small "dark current" that may cause a charge to accumulate within an imaging element that is unrelated to the intensity of radiation (or light) received by the imaging element. This dark current thereby causes errors in the calculated intensity of a radiation field location that is associated with the imaging element.

Offset correction is intended to compensate for dark current effects on acquired images. According to some offset correction techniques, images are acquired at step S201 during a period of non-irradiation, and an average image is then calculated from the acquired images. The average image is known as an offset correction image and is used to modify subsequently-acquired images to compensate for dark current effects as will be described below with respect to step S206. The averaged images are preferably acquired at a same rate as the subsequently-acquired images so as to better approximate the effect of dark current on the subsequently-acquired images. Since the extent of dark current effects may vary across imaging devices, imaging devices are often sold with customized software for performing offset correction.

A gain correction image may also be acquired in step S201 by irradiating imaging device 20 with radiation beam 15 while no object lies between treatment head 11 and imaging device 20. The gain correction image therefore represents differences in sensitivity and gain among pixels of imaging device 20 and also represents differences in intensities of a radiation field produced by radiation beam 15.

Next, in step S202, a first image of a radiation field produced by a radiation beam is acquired. At least a portion of the radiation field is attenuated by a radiation attenuation device, and the first image includes a representation of first scatter radiation. Step S202 may proceed as described above with respect to step S71. In the present example, it will be assumed that step S202 proceeds as illustrated and described with respect to FIG. 4 and FIG. 5.

Figure 9:
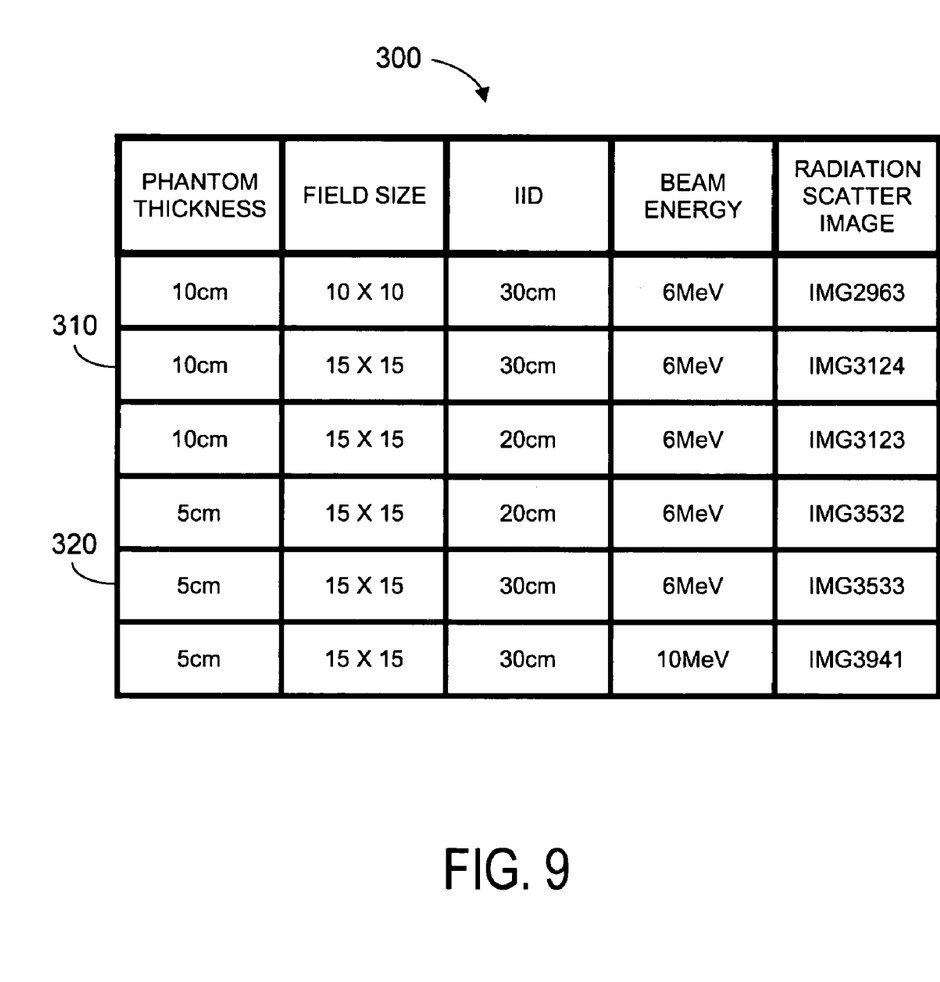
FIG. 9 is a tabular representation of associated device parameters, image acquisition parameters, and radiation scatter images according to some embodiments.

According to some embodiments, the first image is stored in association with radiation attenuation properties of the radiation attenuation device and/or in association with image acquisition parameters according to which the first image was acquired. FIG. 9 is a tabular representation of a portion of database 300. Database 300 may be stored in one or more of linac 10, processor 41, imaging device 20, and another element. Database 300 associates Radiation Scatter Images such as the first image acquired in step S202 with radiation attenuation properties such as Phantom Thickness, and with image acquisition parameters such as Field Size, isocenter to Imager Distance (IID), and Beam Energy.

After some embodiments of step S202, row 310 of database 300 is populated with a thickness of a radiation attenuation device, a radiation field size, an IID and a beam energy used to acquire the first image, as well as with a link to a file including the first image. Database 300 may associate more or fewer radiation attenuation properties and/or image acquisition parameters with a radiation scatter image according to some embodiments.

A second image of a second radiation field produced by a radiation beam is acquired in step S203. A portion of the second radiation field is attenuated by a second radiation attenuation device, and the second image includes a representation of second scatter radiation. Step S203 may proceed as described above with respect to step S202, however with a radiation attenuation device that differs from the radiation attenuation device used in step S202.

Figure 10:
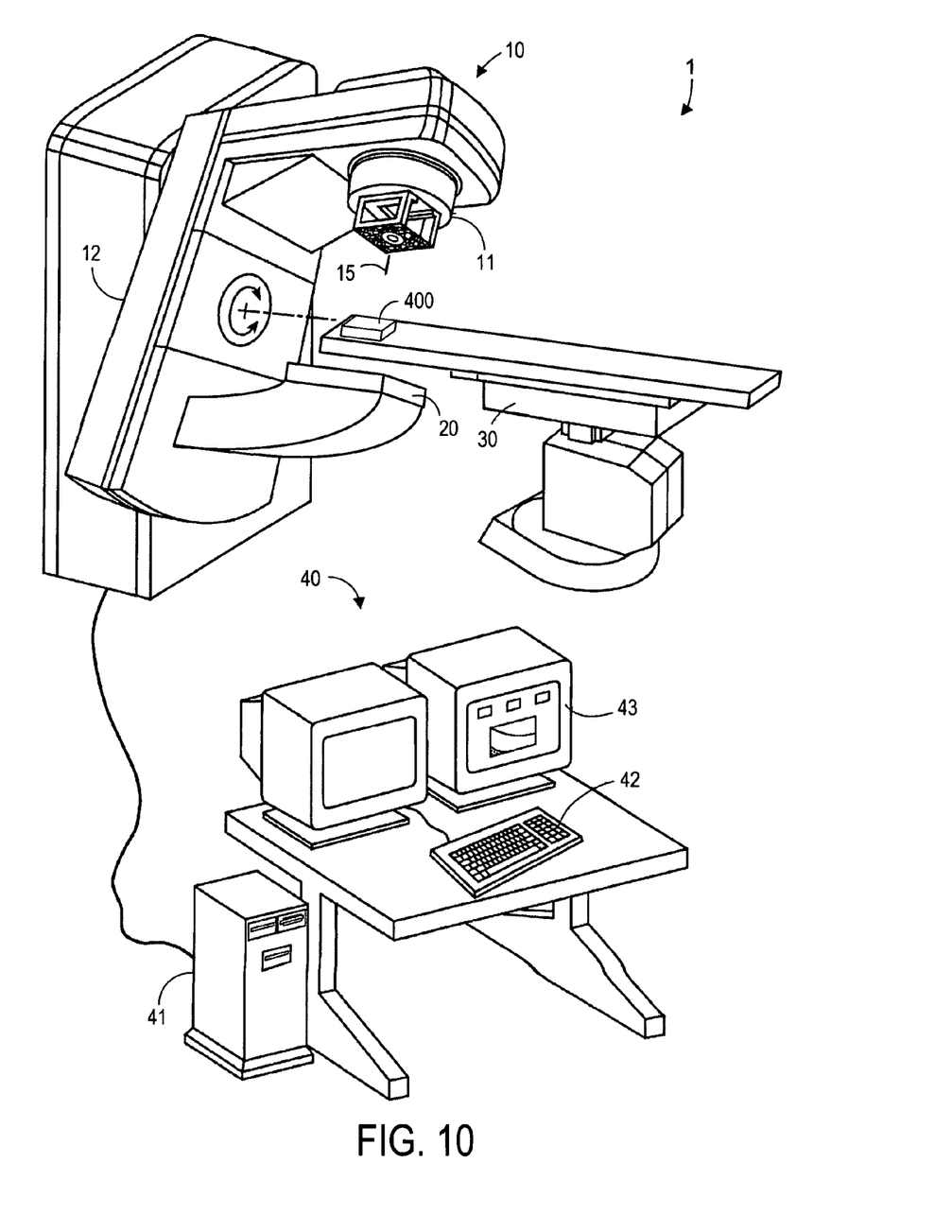
FIG. 10 illustrates acquisition of a second image including a representation of second scatter radiation according to some embodiments.

FIG. 10 illustrates radiation therapy room 1 according to some embodiments of step S203. Linac 10 is shown emitting radiation beam 15 toward radiation attenuation device 400. Gantry 12 may be positioned such that a beam axis of beam 15 is normal to an upper surface of radiation attenuation device 400. Radiation attenuation device 400 is positioned on table 30 between treatment head 11 and imaging device 20, and, in the illustrated embodiment, is thinner than radiation attenuation device 80 used in FIG. 4. Beam 15 produces the second radiation field on a surface of imaging device 20 after being attenuated by radiation attenuation device 400.

Radiation attenuation device 400 may comprise a water phantom having radiation-attentive properties similar to radiation properties of a given volume of tissue. Radiation attenuation device 400 may be composed of material having radiation-attentive properties similar to those of any other volume of interest. As described above, Compton scattering of radiation passing through radiation attenuation device 400 may produce the second scatter X-ray radiation, which may be detected by imaging device 20 during step S203 and may therefore be represented in the acquired second image.

According to some embodiments, a filename of the second image is stored in database 300 in association with radiation attenuation properties of the second radiation attenuation device and image acquisition parameters according to which the second image was acquired. Row 320 includes thusly-stored data according to the present example. As shown, the image acquisition parameters are identical to those used to acquire the first image, but the specified phantom thicknesses are different. In some embodiments, any number of radiation attenuation properties and image acquisition parameters may differ between steps S202 and S203.

Some embodiments of process 800 include acquisition of additional images according to different combinations of image acquisition parameters and using radiation attenuation devices exhibiting different radiation attenuation properties. The additional images may each include a representation of scatter radiation. The different combinations and their associated images may be used to further populate database 300 as shown in FIG. 9.

In some embodiments of step S205, radiation attenuation properties of the subject volume and image acquisition parameters used to acquire the third image are compared to radiation attenuation properties of radiation attenuation devices 80 and 400 and image acquisition parameters used to acquire the first image and the second image. Using currently- or hereafter-known interpolation techniques, relationships between the compared properties and parameters are determined and the relationships are used to generate a reference scatter image based on the representation of first scatter radiation in the first image and the representation of second scatter radiation in the second image. Interpolation in step S205 thereby allows the generation of predicted scatter radiation without having to populate a database such as database 300 with all possible combinations of image acquisition parameters and device attenuation properties.

According to some embodiments, a filename of the second image is stored in database 300 in association with radiation attenuation properties of the second device and image acquisition parameters according to which the second image was acquired. Row 320 includes thusly-stored data according to the present example. As shown, the image acquisition parameters are identical to those used to acquire the first image, but the specified phantom thicknesses are different. In some embodiments, any number of radiation attenuation properties and image acquisition parameters may differ between steps S202 and S203.

Some embodiments of process 800 include acquisition of additional images according to different combinations of image acquisition parameters and using devices exhibiting different radiation attenuation properties. The additional images may each include a representation of scatter radiation. The different combinations and their associated images may be used to further populate database 300 as shown in FIG. 9.

A third image of a third radiation field is then acquired in step S204. The third image is attenuated by a volume and includes a representation of third scatter radiation. Step S204 may proceed as described above with respect to step S72, and the third image may correspond to image 100 of FIG. 6.

Next, in step S205, a reference scatter image is determined by interpolating the representation of the first scatter radiation and the representation of the second scatter radiation. The reference scatter image may include a representation of scatter radiation that may be generated using the volume and image acquisition parameters of step S204.

In some embodiments of step S205, radiation attenuation properties of the subject volume and image acquisition parameters used to acquire the third image are compared to radiation attenuation properties of devices 80 and 400 and image acquisition parameters used to acquire the first image and the second image. Using currently- or hereafter-known interpolation techniques, relationships between the compared properties and parameters are determined and the relationships are used to generate a reference scatter image based on the representation of first scatter radiation in the first image and the representation of first scatter radiation in the second image. Interpolation in step S205 thereby allows the generation of predicted scatter radiation without having to populate a database such as database 300 with all possible combinations of image acquisition parameters and device attenuation properties.

The reference scatter image is associated with one of the correction images in step S206. According to some embodiments, the reference scatter image is added to an offset correction image acquired in step S201. Some embodiments of step S206 comprise linking the reference scatter image to a gain correction image.

In some embodiments of step S207, the third image is modified based on the correction images. Accordingly, the pixel values of the offset correction image (which may have been altered in step S206 according to the reference scatter image) may be subtracted from corresponding pixel values of the third image. Also or alternatively, the gain of each pixel of the third image may be normalized according to the gain correction image. The gain correction image is therefore used to remove intensity variations due to differences in pixel sensitivities of imaging device 20 and differences in radiation intensities of the radiation field produced by radiation beam 15.

In a case that the reference scatter image is linked to the gain correction image, the gain of each pixel of the third image may further be normalized to eliminate any variations that exist in the reference scatter image. These variations may comprise a representation of reference scatter radiation that is substantially similar to the third scatter radiation represented in the third image. Accordingly, the third image may be modified in step S207 so as to compensate for the third scatter radiation.

According to some embodiments of step S207, the gain correction image is also used to identify non-functioning pixels of imaging device 20, or "dead" pixels. An image, or map, is generated based on the identified dead pixels and the map is used to reassign the value of each dead pixel to a value that is based on values of neighboring pixels. The dead pixel map is then used to generate intensity values for inoperative imaging elements of imaging device 20.

Those in the art will appreciate that various adaptations and modifications of the above-described embodiments can be configured without departing from the scope and spirit of the claimed invention. Also, some embodiments differ from the above description. Therefore, it is to be understood that, within the scope of the appended claims, the claimed invention may be practiced other than as specifically described herein.

What is claimed is:

1. A method comprising:
   acquiring a first image of a first radiation field, at least a portion of the first radiation field comprising radiation attenuated by a first device, and the first image including a representation of first scatter radiation generated during acquisition of the first image;
   acquiring a second image of a second radiation field, at least a portion of the second radiation field comprising radiation attenuated by a second device, and the second image including a representation of second scatter radiation generated during acquisition of the second image;
   acquiring a third image of a third radiation field, at least a portion of the third radiation field comprising radiation attenuated by a volume, and the third image including a representation of third scatter radiation generated during acquisition of the third image;
   determining an interpolant comprising a function of radiation attenuation properties and a representation of scatter radiation based on the representation of the second scatter radiation, the representation of the first scatter radiation, radiation attenuation properties of the first device, and radiation attenuation properties of the second device
   determining a reference scatter image based on the interpolant and on radiation attenuation properties of the volume;
   modifying the third image based on the reference scatter image to compensate for the third scatter radiation; and, displaying said modified third image.

2. A method according to claim 1, wherein one or more of the radiation attenuation properties of the first device is different from one or more respective radiation attenuation properties of the second device.

3. A method according to claim 1, wherein one or more image acquisition parameters used to acquire the first image is different from one or more respective image acquisition parameters used to acquire the second image.

4. A method according to claim 1, wherein determining the interpolant is further based on image acquisition parameters used to acquire the first image, and image acquisition parameters used to acquire the second image, and
wherein determining the reference scatter image is further based on image acquisition parameters used to acquire the third image.

5. A method according to claim 1, wherein the first device comprises a water phantom.

6. A method according to claim 1, wherein modifying the third image comprises:
determining a conversion to substantially remove the reference scatter image radiation from the third image; and
applying the conversion to the third image.

7. A method according to claim 6, wherein determining the conversion comprises:
determining a gain for each of a plurality of pixels of the reference scatter image, the gain to cause each of the plurality of pixels to have a single value that is based on values of each of the plurality of pixels of the reference scatter image; and
wherein applying the conversion comprises:
applying the gain to each of a corresponding plurality of pixels of the third image.

8. A method according to claim 6, wherein determining the conversion comprises:
determining a scatter correction value for each of a plurality of pixels of the reference scatter image; and
wherein applying the conversion comprises:
subtracting the scatter correction value from each of a corresponding plurality of pixels of the third image.

9. A medium storing processor-executable process steps, the process steps comprising:
a step to acquire a first image of a first radiation field, at least a portion of the first radiation field comprising radiation attenuated by a first device, and the first image including a representation of first scatter radiation generated during acquisition of the first image;
a step to acquire a second image of a second radiation field, at least a portion of the second radiation field comprising radiation attenuated by a second device, and the second image including a representation of second scatter radiation generated during acquisition of the second image;
a step to acquire a third image of a third radiation field, at least a portion of the third radiation field comprising radiation attenuated by a volume, and the third image including a representation of third scatter radiation generated during acquisition of the third image;
a step to determine an interpolant comprising a function of radiation attenuation properties and a representation of scatter radiation based on the representation of the second scatter radiation, the representation of the first scatter radiation, radiation attenuation properties of the first device, and radiation attenuation properties of the second device;
a step to determine a reference scatter image based on the interpolant and on radiation attenuation properties of the volume;
a step to modify the third image based on the reference scatter image to compensate for the third scatter radiation; and, a step of displaying said modified third image.

10. A medium according to claim 9, wherein one or more of the radiation attenuation properties of the first device is different from one or more respective radiation attenuation properties of the second device.

11. A medium according to claim 9, wherein one or more image acquisition parameters used to acquire the first image is different from one or more respective image acquisition parameters used to acquire the second image.

12. A medium according to claim 9, wherein the step to determine the interpolant further based on image acquisition parameters used to acquire the first image, and image acquisition parameters used to acquire the second image, and
wherein the step to determine the reference scatter image is further based on image acquisition parameters used to acquire the third image.

13. A medium according to claim 9, wherein the step to modify the third image comprises:
a step to determine a conversion to substantially remove the reference scatter image from the third image; and
a step to apply the conversion to the third image.

14. A medium according to claim 13, wherein the step to determine the conversion comprises:
a step to determine a gain for each of a plurality of pixels of the reference scatter image, the gain to cause each of the plurality of pixels to have a single value that is based on values of each of the plurality of pixels of the reference scatter image; and
wherein the step to apply the conversion comprises:
a step to apply the gain to each of a corresponding plurality of pixels of the third image.

15. A medium according to claim 13, wherein the step to determine the conversion comprises:
a step to determine a scatter correction value for each of a plurality of pixels of the reference scatter image; and
wherein the step to apply the conversion comprises:
a step to subtract the scatter correction value from each of a corresponding plurality of pixels of the third image.

16. An apparatus comprising:
a memory storing processor-executable process steps;
an imaging device to acquire images of radiation fields; and
a processor in communication with the memory and operative in conjunction with the stored process steps to:
control the imaging device to acquire a first image of a first radiation field, at least a portion of the first radiation field comprising radiation attenuated by a first device, and the first image including a representation of first scatter radiation generated during acquisition of the first image;
control the imaging device to acquire a second image of a second radiation field, at least a portion of the second radiation field comprising radiation attenuated by a second device, and the second image including a representation of second scatter radiation generated during acquisition of the second image;
control the imaging device to acquire a third image of a third radiation field, at least a portion of the third radiation field comprising radiation attenuated by a volume, and the third image including a representation of third scatter radiation generated during acquisition of the third image;

determine an interpolant comprising a function of radiation attenuation properties and a representation of scatter radiation based on the representation of the second scatter radiation, the representation of the first scatter radiation, radiation attenuation properties of the first device, and radiation attenuation properties of the second device;

determine a reference scatter image based on the interpolant and on radiation attenuation properties of the volume; and modify the third image based on the reference scatter image to compensate for the third scatter radiation.

17. An apparatus according to claim 16, wherein one or more of the radiation attenuation properties of the first device is different from one or more respective radiation attenuation properties of the second device.

18. An apparatus according to claim 16, wherein one or more image acquisition parameters used to acquire the first image is different from one or more respective image acquisition parameters used to acquire the second image.

19. An apparatus according to claim 16, wherein determination of the interpolant is further based on image acquisition parameters used to acquire the first image, and image acquisition parameters used to acquire the second image, and wherein determination of the reference scatter image is further based on image acquisition parameters used to acquire the third image.

20. An apparatus according to claim 16, wherein modification of the third image comprises:

determination of a conversion to substantially remove the reference scatter image from the third image; and application of the conversion to the third image.

21. An apparatus according to claim 20, wherein determination of the conversion comprises:

determination of a gain for each of a plurality of pixels of the reference scatter image, the gain to cause each of the plurality of pixels to have a single value that is based on values of each of the plurality of pixels of the reference scatter image; and wherein application of the conversion comprises:

application of the gain to each of a corresponding plurality of pixels of the third image.

22. An apparatus according to claim 20, wherein determination of the conversion comprises:

determination of a scatter correction value for each of a plurality of pixels of the reference scatter image; and wherein application of the conversion comprises:

subtraction of the scatter correction value from each of a corresponding plurality of pixels of the third image.

23. A system comprising:

a linear accelerator to emit a radiation beam;

an imaging device to:

acquire a first image of a first radiation field produced by the radiation beam, at least a portion of the first radiation field comprising radiation attenuated by a first device, and the first image including a representation of first scatter radiation generated during acquisition of the first image;

acquire a second image of a second radiation field produced by the radiation beam, at least a portion of the second radiation field comprising radiation attenuated by a second device, and the second image including a representation of second scatter radiation generated during acquisition of the second image; and acquire a third image of a second radiation field produced by the radiation beam, at least a portion of the third radiation field comprising radiation attenuated by a volume, and the third image including a representation of third scatter radiation generated during acquisition of the third image; and a processor to determine an interpolant comprising a function of radiation attenuation properties and a representation of scatter radiation based on the representation of the second scatter radiation, the representation of the first scatter radiation, radiation attenuation properties of the first device, and radiation attenuation properties of the second device, to determine a reference scatter image based on the interpolant and on radiation attenuation properties of the volume, and to modify the third image based on the reference scatter image to compensate for the third scatter radiation.

24. A system according to claim 23, wherein one or more of the radiation attenuation properties of the first device is different from one or more respective radiation attenuation properties of the second device.

25. A system according to claim 23, wherein one or more image acquisition parameters used to acquire the first image is different from one or more respective image acquisition parameters used to acquire the third image.

26. A system according to claim 23, wherein determination of the interpolant is further based on image acquisition parameters used to acquire the first image, and image acquisition parameters used to acquire the second image, and wherein determination of the reference scatter image is further based on image acquisition parameters used to acquire the third image.

27. A system according to claim 23, wherein modification of the third image by the processor comprises:

determination of a conversion to substantially remove the reference scatter image from the third image; and application of the conversion to the third image.

28. A system according to claim 27, wherein determination of the conversion comprises:

determination of a gain for each of a plurality of pixels of the reference scatter image, the gain to cause each of the plurality of pixels to have a single value that is based on values of each of the plurality of pixels of the reference scatter image; and wherein application of the conversion comprises:

application of the gain to each of a corresponding plurality of pixels of the third image.

29. A system according to claim 27, wherein determination of the conversion comprises:

determination of a scatter correction value for each of a plurality of pixels of the reference scatter image; and wherein application of the conversion comprises:

subtraction of the scatter correction value from each of a corresponding plurality of pixels of the third image.

* * * * *